(12) United States Patent
Medrano Rupérez et al.

(10) Patent No.: US 8,097,723 B2
(45) Date of Patent: Jan. 17, 2012

(54) PROCESS FOR THE PREPARATION OF ABACAVIR

(75) Inventors: Jorge Medrano Rupérez, Barcelona (ES); Julio Campon Pardo, Barcelona (ES); Laia Elías Rius, Barcelona (ES); Ramón Berenguer Maimó, Barcelona (ES)

(73) Assignee: Esteve Quimica, S.A., Barcelona (ES)

( * ) Notice: Subject to any disclaimer, the term of this patent is extended or adjusted under 35 U.S.C. 154(b) by 316 days.

(21) Appl. No.: 12/520,510

(22) PCT Filed: Dec. 20, 2007

(86) PCT No.: PCT/EP2007/064371
§ 371 (c)(1),
(2), (4) Date: Jun. 19, 2009

(87) PCT Pub. No.: WO2008/074874
PCT Pub. Date: Jun. 26, 2008

(65) Prior Publication Data
US 2010/0041883 A1    Feb. 18, 2010

Related U.S. Application Data

(60) Provisional application No. 60/871,347, filed on Dec. 21, 2006.

(30) Foreign Application Priority Data

Dec. 21, 2006  (EP) ..................... 06126797

(51) Int. Cl.
*C07D 473/16*    (2006.01)
*C07D 473/40*    (2006.01)

(52) U.S. Cl. .................................... 544/277

(58) Field of Classification Search .............. 544/277
See application file for complete search history.

(56) References Cited

U.S. PATENT DOCUMENTS

| | | | |
|---|---|---|---|
| 2010/0004446 A1* | 1/2010 | Medrano Ruperez et al. | 544/277 |
| 2010/0137592 A1* | 6/2010 | Sayyed et al. | 544/277 |

FOREIGN PATENT DOCUMENTS

| | | |
|---|---|---|
| EP | 0434450 A2 | 6/1991 |
| EP | 0921121 A1 | 6/1999 |
| WO | WO9521161 A1 | 8/1995 |
| WO | W02005023811 A1 | 3/2005 |
| WO | WO 2008072074 A1 * | 6/2008 |

OTHER PUBLICATIONS

Izawa, Journal of the Chemical Society, Perkin Transactions 1: Organic and Bio-Organic Chemistry (1972-1999), (1992), (19), 2519-25.*

Daluge, Susan M. et al., An Efficient, Scalable Synthesis of the HIV Reverse Transcriptase Inhibitor Ziagen, Nucleosides, Nucleotides & Nucleic Acids, Jan.-Feb. 2000, pp. 297-327, vol. 19, Issue 1&2, Marcel Dekker Inc., USA.

* cited by examiner

*Primary Examiner* — Mark Berch
(74) *Attorney, Agent, or Firm* — Peter B. Scull; K M Kalan; Berenbaum Weinshienk PC

(57) ABSTRACT

Process for the preparation of abacavir, or its salts or its solvates comprising the step of reacting a compound (IV) where $R_1$ is a $(C_1\text{-}C_4)$-alkyl radical with anhydrous hydrochloric acid/$(C_1\text{-}C_6)$-alcohol, and then with tri$(C_1\text{-}C_4)$-alkyl orthoformate, in the absence of water. The preparation process may include further steps of reacting the compound obtained with cyclopropylamine and subsequently hydrolysis to yield abacavir.

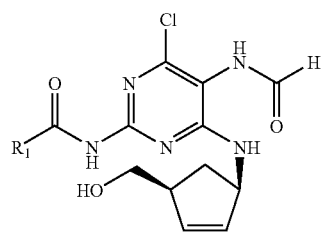

(IV)

15 Claims, No Drawings

PROCESS FOR THE PREPARATION OF ABACAVIR

CROSS-REFERENCE TO RELATED APPLICATIONS

The present application is the US national stage application of the Patent Cooperation Treaty (PCT) Application Number PCT/EP2007/064371, filed 20 Dec. 2007, entitled "PROCESS FOR THE PREPARATION OF ABACAVIR"; which designated the United States of America, inter alia; and which claims priority from the European Patent Application, Number 06126797.7, filed 21 Dec. 2006, and from the U.S. Provisional Patent Application, No. 60/871,347, also filed 21 Dec. 2006, the subject matter of each of which hereby being specifically incorporated herein by reference for all that they disclose and teach.

The invention refers to a process for the preparation of an active pharmaceutical ingredient known as abacavir. The process is based on the formation of the purine ring using specific conditions.

BACKGROUND ART

Abacavir, is the International Nonproprietary Name (INN) of {(1S,4R)-4-[2-amino-6-(cyclopropylamino)-9H-purin-9-yl]-cyclopent-2-enyl}methanol, and CAS No. 136470-78-5. Abacavir sulfate is a potent selective inhibitor of HIV-1 and HIV-2, and can be used in the treatment of human immunodeficiency virus (HIV) infection.

The structure of abacavir hemisulfate salt corresponds to formula (I):

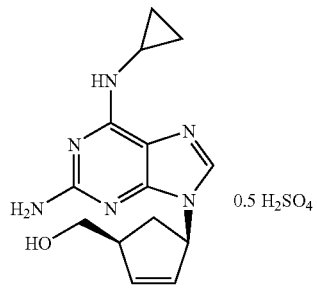

(I)

EP 434450-A discloses certain 9-substituted-2-aminopurines including abacavir and its salts, methods for their preparation, and pharmaceutical compositions using these compounds.

Different preparation processes of abacavir are known in the art. In some of them abacavir is obtained starting from an appropriate pyrimidine compound, by a process comprising a coupling reaction of said compound or a later intermediate with a sugar analogue residue, a cyclisation to form the imidazole ring and the introduction of the cyclopropylamino group at the 6 position of the purine ring.

Several methods to perform the cyclisation of intermediates of abacavir are described in the art. According to EP 434450-A, the cyclisation of several intermediates of abacavir, including the following intermediates where R is cyclopropylamino or chloride,

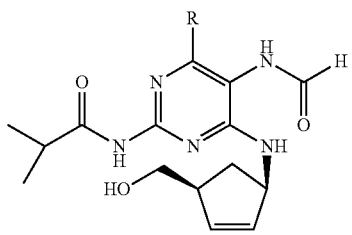

is carried out using formic acid or a reactive formic acid derivative, optionally in the presence of a cosolvent and a strong anhydrous acid such as ethanesulfonic acid. There is not an specific example where the cyclisation is carried out in the presence of an anhydrous acid. Example 27 illustrates the cyclisation of (+)-(1R,4S)-cis-N-[4-chloro-5-formamido-6-{[4-(hydroxymethyl)-2-cyclopentene-1-yl]amino}-2-pyrimidinyl]isobutyramide, using triethyl orthoformate and concentratre aqueous hydrochloric acid, thereby the amino group at 5 position of the pyrimidine is hydrolysed and the compound is cyclised. The main disadvantage is the formation of several by-products, affecting the yield and the purity of the compound obtained.

EP 741710-A describes the cyclisation of the N-{2-amino-4-chloro-6-[(1R,4S)-4-(hydroxymethyl)cyclopent-2-enylamino]pyrimidin-5-yl}formamide of the following formula,

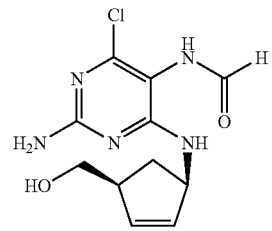

using the same cyclisation conditions as the previous patent application, i.e. triethyl orthoformate and concentrate hydrochloric acid.

The same authors of both patents applications state in a later publication (cf. S. M. Daluge et al., Nucleosides, Nucleotides & nucleic acids 2000, vol. 19, pp. 297-327) that the cyclisation of N-{2-amino-4-chloro-6-[(1R,4S)-4-(hydroxymethyl)cyclopent-2-enylamino]pyrimidin-5-yl}formamide, occurred smoothly in triethyl orthoformate and concentrated aqueous hydrochloric acid, but it could not be cyclised in ethyl orthoformate with anhydrous acids, e.g. ethanesulfonic acid, concentratred sulfuric acid, or anhydrous hydrochloric acid. According to this document, the rapid formation of the cyclic compound using concentrated aqueous hydrochloric acid suggests that the conformation of the starting material may be unfavourable for cyclisation and that the addition of water disrupt internal H-bonds and facilitate cyclisation.

WO 2005/023811 describes the cyclisation of [(1S,4R)-4-(2,5-diamino-6-chloropyrimidin-4-ylamino)cyclopent-2-enyl]methanol of the following formula,

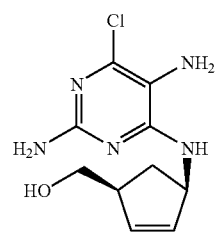

using triethyl orthoformate and a catalytic amount of anhydrous or concentrated hydrochloric acid, being the cyclisation preferably carried out in an aprotic apolar solvent. Unlike the starting material of the patent applications mentioned above, in this case the amino groups at 2 and 5 position are not protected.

Despite the teaching of this prior art documents, the research of new cyclisation processes of intermediates of abacavir, in particular intermediates having the amino group at 2- and 5-position of the pyrimidine protected with an acyl group, is still an active field, since the known processes proceed with low yield and purity, as it has been pointed out above. Thus, the provision of a new process for the cyclisation of said intermediates of abacavir to give the purine structure is desirable.

SUMMARY OF THE INVENTION

Inventors have found that the cyclisation of the pyrimidine intermediate of abacavir, N-{4-chloro-5-formamido-6-[(1R,4S)-4-(hydroxymethyl)cyclopent-2-enylamino]pyrimidin-2-yl}isobutyramide, proceeds with high yield and without significant formation of by-products when a solution of anhydrous hydrochloric acid/isopropanol and tritethyl orthoformate, in the absence of water, is used. The process comprises the removal of the formyl group of the 5-amino group of the pyrimidine by solvolysis in the absence of water, and the cyclisation of the compound obtained using a cyclising agent such as triethyl orthoformate. It is surprising that, unlike what is stated in the art, the cyclisation occurs efficiently using an anhydrous acid. The presence of an alcohol allows to carry out the deprotection/cyclisation avoiding the drawbacks of the known methods, forming the purine ring with high yield and high purity.

Thus, the present invention refers to the provision of a process for the preparation of abacavir of formula (I) or its pharmaceutically acceptable salts, or its solvates,

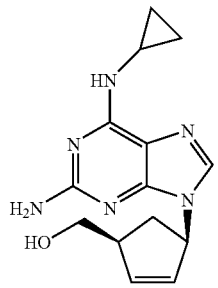

(I)

comprising the step of ring closure of the compound of formula (IV) by first reacting said compound of formula (IV) with a solution of anhydrous hydrochloric acid in a $(C_1-C_6)$-alcohol, and then with tri$(C_1-C_4)$-alkyl orthoformate, in the absence of water, to yield a compound of formula (III), wherein $R_1$ is a $(C_1-C_4)$-alkyl radical;

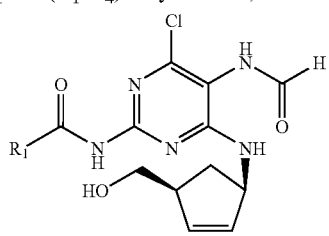

(IV)

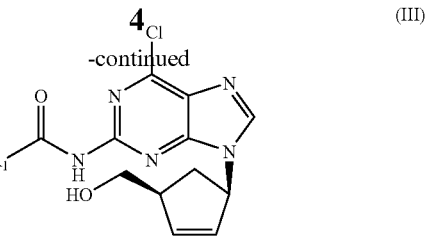

(III)

Among the striking advantageous features of the process of the present invention, the following can be mentioned: (i) the cyclisation carried out in said anhydrous conditions is more efficient; (ii) lower formation of impurities; in the reaction conditions of the present invention the solvolysis takes place with a low formation of by-products; (iii) it takes place without racemization; (iv) less quantity of cyclising agent is needed; and (v) shorter reaction times are required.

DETAILED DESCRIPTION OF THE INVENTION

In a particular embodiment of the present invention, the process for the preparation of abacavir (I) or its pharmaceutically acceptable salts, or its solvates, comprises the ring closure of the compound of formula (IV) with $R_1$=isopropyl, i.e. N-{4-chloro-5-formamido-6-[(1R,4S)-4-(hydroxymethyl)cyclopent-2-enylamino]pyrimidin-2-yl}isobutyramide of formula (IVa).

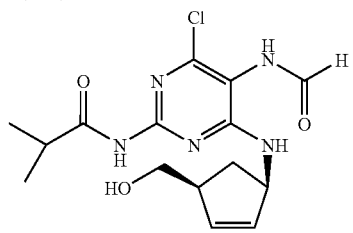

(IVa)

In a preferred embodiment, the ring closure of the compound of formula (IV) is carried out by first reacting said compound (IV) with a solution of anhydrous hydrochloric acid in isopropanol to remove the formyl group of the amino at 5-position of the pyrimidine, and then with triethyl orthoformate.

Generally the solvolysis reaction to remove the amino protecting group of the 5-amino group is carried out with an excess of hydrochloric acid. Generally, between 1-25 mol of a solution of hydrochloric acid/alcohol per mol of starting material is used. In a preferred embodiment, the molar ratio is 6:1. Preferably, the solvolysis reaction is carried out at a temperature comprised between room temperature (approximately 20-25° C.) and reflux. More preferably, the reaction is carried out between about 30-50° C.

Generally, the reaction with the tri$(C_1-C_4)$-alkyl orthoformate is carried out at a temperature comprised between about 0° C. and 30° C. More preferably, at a temperature comprised between 5-10° C. In a preferred embodiment, the amount of cyclisating agent is between 2-5 mol of cyclisating agent per mol of starting material.

Although the solution of anhydrous hydrochloric acid in $(C_1-C_6)$-alcohol and the tri$(C_1-C_4)$-alkyl orthoformate can be added simultaneously, best results are obtained when the solution of anhydrous hydrochloric acid in $(C_1-C_6)$-alcohol and the tri$(C_1-C_4)$-alkyl orthoformate are added sequentially. Thus, in a particular embodiment, after adding the solution of anhydrous hydrochloric acid in isopropanol, the reaction mixture is stirred for at least 10 minutes before adding the triethyl orthoformate. Preferably, the mixture is stirred about 2 hours before adding the triethyl orthoformate.

As it is shown in the examples, when the cyclisation is carried out in the absence of water, the yield is tremendously increased and also the chemical purity of the compound obtained. Furthermore, the amount of cyclising agent is significantly reduced.

The compound of formula (IVa) can be prepared as described in Example 23 of the European patent application EP 921121-A. Compounds of formula (IV) can be prepared analogously.

In a preferred embodiment the preparation process of abacavir or its pharmaceutically acceptable salts or its solvates mentioned above, further comprises the following steps:
(i) reacting the compound of formula (III) with cyclopropylamine to yield a compound of formula (II) wherein $R_1$ is a $(C_1-C_4)$-alkyl radical;

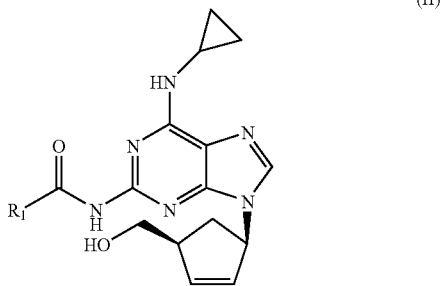

(II)

(ii) hydrolysing the amide of formula (II) to yield abacavir (I) or a salt thereof; and, if desired, abacavir (I) in free form is converted into a salt, or a salt of the abacavir (I) obtainable according to the process is converted into the free abacavir (I) or into another salt.

Thus, the compound of formula (III) above obtained after the cyclisation step may for example be converted into abacavir by reaction with cyclopropylamine, generally in the presence of a base and a suitable solvent, followed by the hydrolysis of the compound obtained to yield abacavir or its salts. The hydrolysis can be carried out in acidic conditions, as described, for instance, in Example 28 of the European paten application EP 434450-A.

The abacavir can be isolated from the reaction medium as a pharmaceutically acceptable salt, preferably the hemisulfate salt. The hemisulfate salt of {(1S,4R)-4-[2-amino-6-(cyclopropylamino)-9H-purin-9-yl]-cyclopent-2-enyl}methanol I means the salt formed between {(1S,4R)-4-[2-amino-6-(cyclopropylamino)-9H-purin-9-yl]-cyclopent-2-enyl}methanol and sulfuric acid in a stoichiometric ratio of 2:1. Alternatively, the compound of formula (I) can be isolated from the reaction medium as a free base. When a pharmaceutically acceptable salt is desired, it can also be obtained from the abacavir base by treatment with the corresponding acid. A preferred salt is the hemisulfate salt of abacavir obtained by treatment of abacavir base with sulfuric acid in a stoichiometric ratio of 2:1. Alternatively, a salt of the abacavir (I) obtainable according to the process is converted into another salt.

The most adequate conditions for carrying out said process vary depending on the parameters considered by an expert in the art, such as, for example, the concentration of the reaction mixture, the temperature, the solvent used during the reaction and the isolation of the product, and the like. These can be readily determined by said skilled person in the art with the help of the teachings of the examples given in this description.

Throughout the description and claims the word "comprise" and variations of the word, are not intended to exclude other technical features, additives, components, or steps. The abstract of this application is incorporated herein as reference. Additional objects, advantages and features of the invention will become apparent to those skilled in the art upon examination of the description or may be learned by practice of the invention.

EXAMPLES

Example Comparative 1

Preparation of (−)-N-[6-(cyclopropylamino)-9-[(1R, 4S)-4-(hydroxymethyl)cyclopent-2-enyl]-9H-purin-2-yl]isobutyramide Using Aqueous HCl Under nitrogen atmosphere N-{4-chloro-5-formamido-6-[(1R,4S)-4-(hydroxymethyl)cyclopent-2-enylamino]pyrimidin-2-yl}isobutyramide (2.0 g, 5.65 mmol) was dissolved in isopropanol (14 ml) and HCl 35% (3 ml, 33.92 mmol). The mixture was heated at 40-42° C. for 2 h. The resulting solution was cooled to 8-10° C., then triethyl orthoformate (2.8 ml, 16.95 mmol) was added and the reaction mixture was stirred at the same temperature for 2 h. HPLC analysis showed no reaction, then additional triethyl orthoformate (21.6 ml, 130 mmol) was added and stirred at 8-10° C. for 2 more hours. NaHCO$_3$ (2.9 g, 33.92 mmol) was added slowly, stirred 30 min and the salts were filtered off.

To the resulting clear solution, NaHCO$_3$ (475 mg, 5.65 mmol) and cyclopropylamine (2 ml, 28.3 mmol) were added, the mixture was refluxed for 1 h and the salts were filtered off. The filtrate was evaporated, isopropanol (10 ml) was added and concentrated twice to dryness. The syrup was dissolved in hot isopropanol (15 ml). This mixture was cooled to 0-2° C. and the resulting slurry filtered off. The solid was dried under vacuum at 30° C. There was obtained 0.428 g (21%) of (−)-N-{6-(cyclopropylamino)-9-[(1R,4S)-4-(hydroxymethyl)cyclopent-2-enyl]-9H-purin-2-yl}isobutyramide as a pink powder. HPLC analysis: 87.7%+5.1% Abacavir.

Example 1

Preparation of (−)-N-{6-(cyclopropylamino)-9-[(1R, 4S)-4-(hydroxymethyl)cyclopent-2-enyl]-9H-purin-2-yl}isobutyramide Using an isopropanolic Solution of HCl Under nitrogen atmosphere, N-{4-chloro-5-formamido-6-[(1R,4S)-4-(hydroxymethyl)cyclopent-2-enylamino]pyrimidin-2-yl}isobutyramide (20.0 g, 56.53 mmol) was dissolved in an anhydrous solution of HCl/isopropanol 2M (170 ml, 339.17 mmol). The mixture was heated at 40-42° C. for 2 h. The resulting solution was cooled to 8-10° C., then triethyl orthoformate (28.2 ml, 169.59 mmol) was added and the reaction mixture was stirred at the same temperature for 2 h. NaHCO$_3$ (28.50 g, 339.17 mmol) was added slowly, stirred 30 min and the salts were filtered off. To the resulting clear solution, NaHCO$_3$ (4.75 g, 56.53 mmol) and cyclopropylamine (19.6 ml, 282.65 mmol) were added, the mixture was refluxed for 1 h and the salts were filtered off. The solution was evaporated and the syrup was dissolved in hot isopropanol (200 ml). This mixture was cooled to 0-2° C. and the resulting slurry filtered off. The solid was dried under vacuum at 30° C. There was obtained 14.42 g (72%) of (−)-N-{6-(cyclopropylamino)-9-[(1R,4S)-4-(hydroxymethyl)cyclopent-2-enyl]-9H-purin-2-yl}isobutyramide as a white powder. HPLC analysis: 94.4%+4.0% Abacavir.

Example 2

Preparation of (−)-N-[6-(cyclopropylamino)-9-[(1R, 4S)-4-(hydroxymethyl)cyclopent-2-enyl]-9H-purin-2-yl]isobutyramide Under nitrogen atmosphere, N-{4-chloro-5-formamido-6-[(1R,4S)-4-(hydroxymethyl)cyclopent-2-enylamino]pyrimidin-2-yl}isobutyramide (15 mg, 42.4 mmol) was dissolved in an anhydrous solution of isopropanol/HCl 1 N (254 ml, 254.4 mmol) and heated to 40-42° C. for 3.5 h. The solution was cooled to 5/10° C. and triethyl orthoformate (21 ml, 127.2 mmol) was added. The resulting mixture was stirred for 2 h at 5-10° C. NaHCO$_3$ (21.37 g, 254.4 mmol) was added slowly, stirred 30 min and the salts were filtered off. To the resulting clear solution, NaHCO$_3$ (3.56 g, 42.4 mmol) and cyclopropylamine (14.7 ml, 212 mmol) were added, the mixture was refluxed for 1 h and the salts were filtered off. The solution was evaporated and the syrup was dissolved in hot isopropanol (120 ml). This mixture was cooled to 0-2° C. and the resulting slurry filtered off. The solid was dried under vacuum at 30° C. There was obtained 10.97 g (73%) of (−)-N-{6-(cyclopropylamino)-9-[(1R,4S)-4-(hydroxymethyl)cyclopent-2-enyl]-9H-purin-2-yl}isobutyramide as a white powder. HPLC analysis: 95.0%+3.8% Abacavir.

Example 3

Preparation of Abacavir Hemisulfate

N-{6-(cyclopropylamino)-9-[(1R,4S)-4-(hydroxymethyl)cyclopent-2-enyl]-9H-purin-2-yl}isobutyramide (6.56 g, 18.40 mmol) was slurried in a mixture of isopropanol (32.8 ml) and 10% solution of NaOH (36.1 ml, 92.0 mmol). The mixture was refluxed for 1 h. The resulting solution was cooled to 20-25° C. and tert-butyl methyl ether (32.8 ml) was added. The layers were separated and H$_2$SO$_4$ 96% (0.61 ml, 11.03 mmol) was added dropwise to the organic layer. This mixture was cooled to 0-5° C. and the resulting slurry filtered off. The solid was dried under vacuum at 40° C. Abacavir hemisulfate (5.98 g, 97%) was obtained as a white powder.

Example 4

Preparation of Abacavir Hemisulfate

N-{6-(cyclopropylamino)-9-[(1R,4S)-4-(hydroxymethyl)cyclopent-2-enyl]-9H-purin-2-yl)}isobutyramide (6.56 g, 18.40 mmol) was slurried in a mixture of isopropanol (32.8 ml) and 10% solution of NaOH (36.1 ml, 92.0 mmol). The mixture was refluxed for 1 h. The resulting solution was cooled to 20-25° C. and toluene (32.8 ml) was added. The layers were separated and H$_2$SO$_4$ 96% (0.61 ml, 11.03 mmol) was added dropwise to the organic layer. This mixture was cooled to 0-5° C. and the resulting slurry filtered off. The solid was dried under vacuum at 40° C. Abacavir hemisulfate (5.42 g, 88%) was obtained as a white powder.

Example 5

Preparation of Abacavir

N-{6-(cyclopropylamino)-9-[(1R,4S)-4-(hydroxymethyl)cyclopent-2-enyl]-9H-purin-2-yl}isobutyramide (1.0 g, 2.80 mmol) was slurried in a mixture of isopropanol (2 ml) and 10% solution of NaOH (1.1 ml, 2.80 mmol). The mixture was refluxed for 1 h. The resulting solution was cooled to 20-25° C. and tert-butyl methyl ether (2 ml) was added. The aqueous layer was discarded, the organic phase was cooled to 0-5° C. and the resulting slurry filtered off. The solid was dried under vacuum at 40° C. Abacavir (0.62 g, 77%) was obtained as a white powder.

The invention claimed is:

1. A process for the preparation of abacavir of formula (I), or a pharmaceutically acceptable salt thereof,

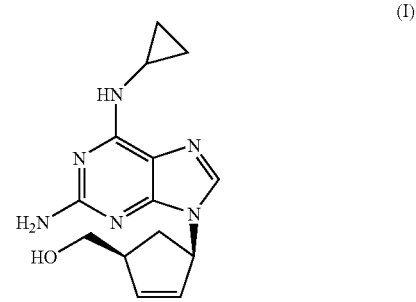

(I)

comprising the step of:
(a) ring closure of the compound of formula (IV) by first reacting said compound (IV) with anhydrous hydrochloric acid/(C$_1$-C$_6$)-alcohol, and then with tri(C$_1$-C$_4$)-alkyl orthoformate, in the absence of water, to yield compound of formula (III),

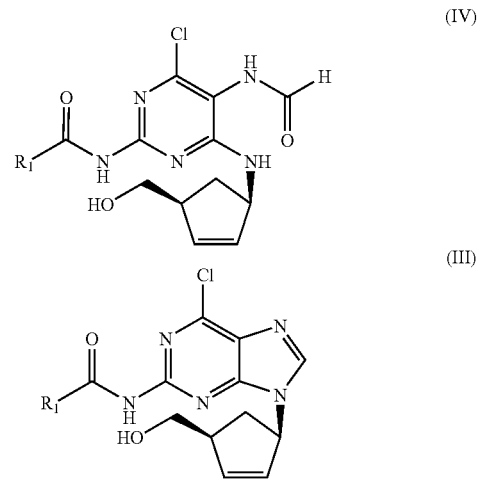

(IV)

(III)

wherein R$_1$ is a (C$_1$-C$_4$)-alkyl radical;-

(b) reacting the compound of formula (III) with cyclopropylamine to yield the compound of formula (II)

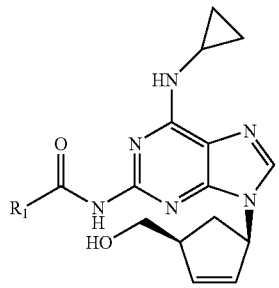

wherein $R_1$ is a $(C_1$-$C_4)$-alkyl radical; and, (c) hydrolyzing the compound of formula (II) to yield abacavir (I) or a salt thereof.

2. The preparation process according to claim 1, wherein $R_1$ is isopropyl.

3. The preparation process according to claim 1, wherein the $(C_1$-$C_6)$-alcohol is isopropanol.

4. The preparation process according to claim 1, wherein the tri$(C_1$-$C_4)$-alkyl orthoformate is triethyl orthoformate.

5. The preparation process according to claim 1, wherein the reaction with the solution of anhydrous hydrochloric acid/$(C_1$-$C_6)$-alcohol is carried out at a temperature between room temperature and reflux and the following reaction with tri$(C_1$-$C_4)$-alkyl orthoformate is carried out at a temperature between 0° C. and 30° C.

6. The preparation process according to claim 1 wherein abacavir (I) in free form is converted into a salt or a salt of abacavir (I) obtainable according to the process of claim 1 is converted into free abacavir (I) or into another salt.

7. The preparation process according to claim 2, wherein the $(C_1$-$C_6)$-alcohol is isopropanol.

8. The preparation process according to claim 2, wherein the tri$(C_1$-$C_4)$-alkyl orthoformate is triethyl orthoformate.

9. The preparation process according to claim 7, wherein the tri$(C_1$-$C_4)$-alkyl orthoformate is triethyl orthoformate.

10. The preparation process according to claim 9, wherein the reaction with the solution of anhydrous hydrochloric acid/$(C_1$-$C_6)$-alcohol is carried out at a temperature between room temperature and reflux and the following reaction with tri$(C_1$-$C_4)$-alkyl orthoformate is carried out at a temperature between 0° C. and 30° C.

11. The preparation process according to claim 2 wherein abacavir (I) in free form is converted into a salt or a salt of abacavir (I) obtainable according to the process of claim 2 is converted into free abacavir (I) or into another salt.

12. The preparation process according to claim 9, further comprising the following steps:

(i) reacting the compound of formula (III)

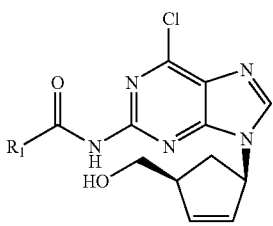

with cyclopropylamine to yield compound of formula (II)

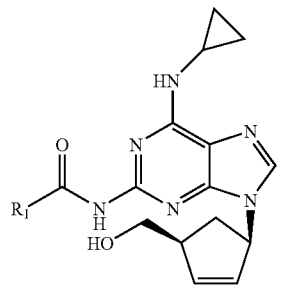

wherein $R_1$ is isopropyl; and, (ii) hydrolysing the compound of formula (II) to yield abacavir (I) or a salt thereof.

13. The preparation process according to claim 12 wherein abacavir (I) in free form is converted into a salt or a salt of abacavir (I) obtainable according to the process of claim 12 is converted into free abacavir (I) or into another salt.

14. The preparation process according to claim 10, further comprising the following steps:

(i) reacting the compound of formula (III)

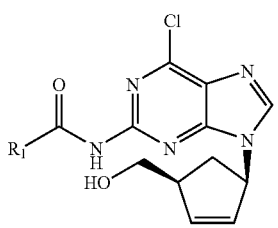

with cyclopropylamine to yield compound of formula (II)

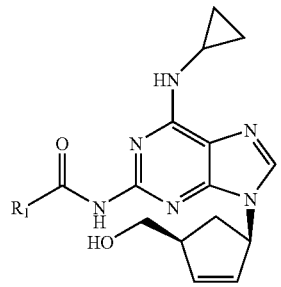

wherein $R_1$ is isopropyl; and, (ii) hydrolysing the compound of formula (II) to yield abacavir (I) or a salt thereof.

15. The preparation process according to claim 14 wherein abacavir (I) in free form is converted into a salt or a salt of abacavir (I) obtainable according to the process of claim 14 is converted into free abacavir (I) or into another salt.

* * * * *